ns Patent [19]

Hendricks et al.

[11] 4,128,558
[45] Dec. 5, 1978

[54] N(O,O DIALKYLPHOSPHONYL ALKYLENE) ESTERS OF OXAZOLIDONE, BENZOXAZOLINONE AND DIHYDROOXAZINONE

[75] Inventors: Udo W. Hendricks, Cologne; Klaus Walz, Leverkusen, both of Germany

[73] Assignee: Bayer Aktiengesellschaft, Leverkusen, Germany

[21] Appl. No.: 595,284

[22] Filed: Jul. 11, 1975

[30] Foreign Application Priority Data

Jul. 17, 1974 [DE] Fed. Rep. of Germany ....... 2434312

[51] Int. Cl.² ................. C07D 263/04; C07D 265/04; C07D 273/02
[52] U.S. Cl. .......................... 260/307 C; 260/239.3 R; 260/326.61; 260/326.45; 106/15 FP; 252/8; 544/97; 546/24
[58] Field of Search ........... 260/307 A, 307 C, 244 R; 544/97

[56] References Cited

U.S. PATENT DOCUMENTS 3,166,565  1/1965  Rigterink ......................... 260/307 H
3,562,288  2/1971  Scherer et al. .................. 260/307 H

FOREIGN PATENT DOCUMENTS 1005372  9/1965  United Kingdom ................ 260/307 C

*Primary Examiner*—Donald G. Daus
*Assistant Examiner*—D. B. Springer

*Attorney, Agent, or Firm*—Plumley and Tyner

[57] ABSTRACT

Phosphonic acid esters of the formula

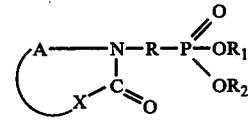

in which
R$_1$ and R$_2$ represent optionally halogen-substituted alkyl or together with —O—P—O— form a five-membered to seven-membered heterocyclic structure,
X represents oxygen or

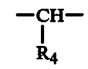

wherein
R$_4$ represents hydrogen or alkyl,
R represents alkylene with 1 – 4 carbon atoms and
A represents alkylene or 1,2-phenylene, which is optionally substituted by halogen, alkyl or halogenoalkyl and is required to complete a five-membered to seven-membered ring system, are suitable as flameproofing agents for textiles, plastics and paper.

6 Claims, No Drawings

N(O,O DIALKYLPHOSPHONYL ALKYLENE) ESTERS OF OXAZOLIDONE, BENZOXAZOLINONE AND DIHYDROOXAZINONE

The invention relates to new phosphonic acid esters of the general formula

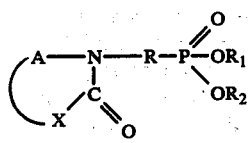  I in which
R₁ and R₂ independently of one another represent an optionally halogen-substituted alkyl radical or together with the oxygen atoms and the phosphorus atom form a five-membered to seven-membered heterocyclic structure,
X represents an oxygen atom or the radical

wherein
R₄ represents hydrogen or an alkyl radical,
R represents an optionally branched alkylene radical with 1–4 carbon atoms and
A represents an alkylene or 1,2-phenylene radical, which is optionally substituted by halogen or an alkyl or halogenoalkyl radical and is required to complete a five-membered to seven-membered ring system,
processes for their preparation and their use as flameproofing agents for textiles, plastics and paper.

Preferred alkyl radicals R₁ and R₂ are those with 1–18 carbon atoms, especially with 1–4 carbon atoms, Preferred halogen are chlorine and bromine, especially chlorine.

R₁ and R₂ conjointly with the oxygen atoms and the phosphorus atom preferably form a dioxaphospholane, dioxaphosphorinane or dioxaphosphepan ring.

The alkyl radical R₄ preferably has 1–4 carbon atoms.

A and X conjointly with the nitrogen and the carbonyl group in particular form an oxazolidone, benzoxazolinone, dihydro oxazinone, pyrrolidone, piperidone or caprolactam ring.

These rings can for example be substituted by halogen, especially chlorine, alkyl radicals with 1–4 C atoms or halogenoalkyl radicals, especially chloroalkyl radicals, with 1–4 C atoms.

Preferred compounds of the formula (I) are those in which
R represents an optionally branched alkylene radical with 2–4 carbon atoms
Amongst these compounds those
in which
A represents the 1,2-ethylene, 1,2-propylene or 1,4-butylene radical
should be singled out.

Further preferred compounds of the formula (I) are those
in which
X represents the radical —CH(R₄)— and
R represents methylene;
those in which
R represents the 1,2-ethylene radical,
R₁ and R₂ represent the methyl, ethyl or 2-chloroethyl radical,
X represents the methylene radical or an oxygen atom and
A represents the 1,2-ethylene, 1,2-propylene or 1,4-butylene radical;
and those in which
R represents methylene, R₁ and R₂ represent the methyl, ethyl or 2-chloroethyl radical,
X represents the methylene radical and
A represents the 1,2-ethylene, 1,2-propylene or 1,4-butylene radical.

The compound of the formula

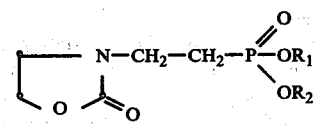

in which
R₁ and R₂ represent the methyl or ethyl radical should be singled out particularly.

The compounds of the formula I can be prepared in accordance with several processes.

PROCESS A

Compounds of the formula

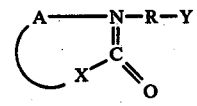  II in which
A, R and X have the abovementioned meaning and
Y represents the hydroxyl, dimethylamino or diethylamino group, the acetoxy or propionyloxy radical or, preferably, a halogen atom, especially a chlorine atom,
are reacted with phosphorous acid trialkyl esters of the formula

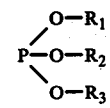  III in which
R₁ and R₂ have the abovementioned meaning and
R₃ represents an optionally halogen-substituted alkyl radical,
if appropriate in the presence of an inert diluent, at temperatures of 40°–210° C.

Compounds of the formula II,
in which
R denotes methylene
are in general preferably reacted at 40°–160° C., especially at 60°–130° C., but for those compounds in which an acetoxy or propionyloxy group is bonded via a methylene group, reaction temperatures of 90–150 have proved advantageous.

Compounds of the formula II,
in which

R denotes an alkylene radical with 2–4 C atoms and
Y represents chlorine or bromine are advantageously reacted at 120°–210°, especially at 150°–180° C.

The following may be mentioned as examples of representatives of the phosphorous acid trialkyl esters of the formula III: trimethyl phosphite, triethyl phosphite, dimethylethyl phosphite, triisopropyl phosphite, tri-n-propyl phosphite, dimethyl-n-propyl phosphite, tri-n-butyl phosphite, tri-iso-butyl phosphite, tris-(chloroethyl)-phosphite, tris-(bromoethyl) phosphite, 2-methoxy-1,3-dioxaphospholane and 2-ethoxy-4-methyl-1,3-dioxa-phospholan.

The following may be mentioned as examples of compounds of the formula II: 3-hydroxymethyl-oxazolidone-(2), 3-chloromethyl-oxazolidone-(2), 3-chloromethyl-5-methyl-oxazolidone-(2), 3-chloromethyl-5-chloromethyl-oxazolidone-(2), 3-dimethylaminomethyl- or diethylaminomethyl-oxazolidone-(2), 3-acetoxymethyl-oxazolidone-(2), 3-hydroxymethyl-1,3-dihydro oxazinone-(2), 3-bromomethyl-1,3-dihydro oxazinone-(2), 3-acetoxymethyl-1,3-dihydro oxazonine-(2), 1-hydroxymethyl-pyrrolidone-(2), 1-chloromethyl-pyrrolidone-(2), 1-dimethylaminomethyl-pyrrolidone-(2), 1-chloromethyl-caprolactam, 1-hydroxymethyl-caprolactam, 3-chloromethyl-benzoxazolinone-(2), 3-(2-bromoethyl)-oxazolidone-2, 3-(2-chloroethyl)-oxazolidone-(2), 1-(2-chloroethyl)-pyrrolidone-(2) and 1-(3-bromopropyl)-pyrrolidone-(2).

It is advisable to remove the compounds $R^3$-Y produced during the reaction, for example methyl chloride, ethyl chloride, ethylene chloride or methyl acetate, continuously from the reaction mixture, for example by distillation or by passing a stream of an inert gas into the mixture.

In general, the compounds of the formulae II and III are employed in the molar ratio of 1:1, but the phosphorous acid trialkyl esters III can also be used in slight excess.

Examples of possible diluents which are inert under the reaction conditions are hydrocarbons, such as toluene, xylene and n-nonane, or dimethylformamide.

In a preferred embodiment of the invention, N-chloromethyloxazolidones are reacted with trialkyl phosphites in the manner described above to give N-dialkoxyphosphonomethyloxazolidones.

PROCESS B

Compounds of the formula

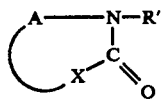
IV in which
A and X have the meaning indicated in formula I and
R' represents an optionally branched $C_2$–$C_4$-alkenyl radical are reacted with phosphorous acid dialkyl esters of the formula

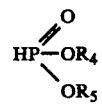
V in which
$R_4$ and $R_5$ independently of one another represent an alkyl radical, or together with the oxygen atoms and the phosphorous atom form a 5-membered to 7-membered heterocyclic structure, in the presence of radical-forming catalysts and, if appropriate, in the presence of inert diluents.

The reaction of the compounds of the formula IV with the phosphorous acid dialkyl esters of the formula V is preferably carried out using excess phosphorous acid dialkyl ester at temperatures of 70°–250° C., preferably 100°–140° C. As radical-forming catalysts it is possible to use organic peroxides, for example dibenzoyl peroxide, di-tert.-butyl peroxide or dicumyl peroxide, or azo compounds, such as azodiisobutyronitrile. The catalysts are employed in amounts of about 0.1–30 mol%, based on the weight of the compounds of the formula IV.

Examples of possible compounds of the formula IV are 1-vinyl-pyrrolidone-2, 1-vinylcaprolactam, 3-vinyl-oxazolidone-2, 3-allyl-oxazolidone-2, 3-methallyl-oxazolidone-2 and 1-allyl-pyrrolidone-2.

As examples of phosphorous acid dialkyl esters of the formula V, dimethyl-phosphite, diethyl phosphite, diisopropyl phosphite, methyl ethyl phosphite, 1,3-dioxa-5,5-dimethyl-2-oxophosphorinane and 1,3-dioxa-2-oxo-phospholane may be mentioned.

PROCESS C

Compounds of the formula

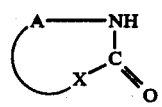
VI in which
A and X have the meaning indicated in formula I are reacted with vinylphosphonic esters of the formula

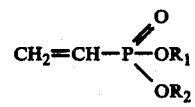
VII in which
$R_1$ and $R_2$ have the meaning mentioned earlier,
if appropriate in the presence of basis catalysts and if appropriate in the presence of inert diluents, at temperatures of 40°–120°, preferably 50°–80°. The addition of minor amounts of polymerisation inhibitors can prove advantageous.

Examples of compounds of the formula VI are pyrrolidone-2, caprolactam-2, oxazolidone-2 and dihydro oxazinone-2, examples of compounds of the formula VII are vinylphosphonic acid dimethyl ester, diethyl ester and diisopropyl ester, vinylphosphonic acid methyl ethyl ester, 1,3-dioxa-2-oxo-2-vinylphospholane and 1,3-dioxa-5,5-dimethyl-2-oxo-2-vinylphosphorinane.

Examples of possible basic catalysts are alkali metals, alkali metal hydroxides, oxides or carbonates or alkaline earth metal hydroxides, oxides or carbonates, alkali metal alcoholates, tertiary amines, such as, for example, triethylamine, pyridine or methyl-piperidine, or quaternary ammonium bases, such as, for example, tetramethylammonium hydroxide or trimethylbenzylammonium hydroxide.

The compounds of the formula I in which R, R₁, R₂, A and X have the meaning indicated in the table which follows may be mentioned as examples of representatives of the compounds according to the invention, of the formula I.

| R | R₁ | R₂ | A | X |
|---|---|---|---|---|
| —CH₂— | CH₃ | CH₃ | —CH₂—CH₂— | —O— |
| —CH₂— | C₂H₅ | C₂H₅ | —CH₂—CH₂— | —O— |
| —CH₂— | —CH(CH₃)₂ | —CH(CH₃)₂ | —CH₂—CH₂— | —O— |
| —CH₂— | —CH₂—CH₂Cl | —CH₂—CH₂Cl | —CH₂—CH₂— | —O— |
| —CH₂—CH₂— | CH₃ | CH₃ | —CH₂—CH₂— | —O— |
| —CH₂—CH₂— | C₂H₅ | C₂H₅ | —CH₂—CH₂— | —O— |
| \>CH—CH₃ | CH₃ | CH₃ | —CH₂—CH₂— | —O— |
| \>CH—CH(CH₃)₂ | C₂H₅ | C₂H₅ | —CH₂—CH₂— | —O— |
| —CH₂—CH₂—CH₂— | CH₃ | CH₃ | —CH₂—CH₂— | —O— |
| —CH₂— | CH₃ | CH₃ | —CH₂—CH₂— | —CH₂— |
| —CH₂— | C₂H₅ | C₂H₅ | —CH₂—CH₂— | —CH₂— |
| —CH₂—CH₂— | CH₃ | CH₃ | —CH₂—CH₂— | —CH₂— |
| —CH₂— | CH₃ | CH₃ | —(CH₂)₃— | —CH₂— |
| —CH₂— | CH₃ | CH₃ | —(CH₂)₄— | —CH₂— |
| —CH₂— | C₂H₅ | C₂H₅ | —(CH₂)₄— | —CH₂— |
| —CH₂— | CH₂CH₂Cl | CH₂CH₂Cl | —(CH₂)₄— | —CH₂— |
| —CH₂—CH₂—CH₂— | CH₃ | CH₃ | —(CH₂)₄— | —CH₂— |

The majority of the compounds according to the invention, of the formula I, are highly viscous, colourless or slightly coloured liquids, or crystalline products.

They are capable of diverse uses, for example as solvents and intermediate products for organic syntheses, for example for the preparation of bactericides, surface-active compounds and textile auxiliaries. In particular, they can be used for the flameproof finishing of fibrous materials consisting of natural or synthetic fibres, and for the flameproof finishing of plastics. For this purpose, compounds of the formula I which are derivatives of oxazolidone have above all proved of value. Using the compounds according to the invention, an outstandingly wash-resistant flameproof finish is achieved on textiles of fibrous materials containing cellulose, such as cotton, linen, viscose or rayon, and especially on textiles of polyester fibres or fibre mixtures containing polyester.

When used as flameproofing agents for textile materials, the phosphonoalkyl derivatives according to the invention, of the formula I, are employed in an amount of about 8 to 60, preferably 10 to 40%, by weight relative to the fibrous material.

For finishing, the textile materials are impregnated with solutions which contain, per liter, about 100 to 400 g of the compounds according to the invention, of the formula I, and optionally further finishing agents, such as creaseproofing agents, softeners, hydrophobic agents and oleophobic agents and acid or latent acid condensation catalysts. The solvent used is preferably water, if appropriate mixed with water-miscible organic solvents, and if appropriate using small amounts of emulsifiers. However, the compounds of the formula I can also be applied to the textile materials from organic solvents, for example hydrocarbons or halogenated hydrocarbons, such as perchloroethylene. The fibrous materials are impregnated with the finishing liquors in a known manner, for example by dipping, padding or spraying, squeezed off to a weight pick-up of about 80-150% and then dried, and thermofixed at 100°-200° C., preferably at 140°-180° C.

By acid hydrolysis of the compounds of the general formula I,

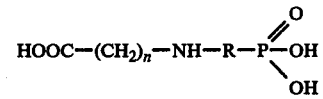

in which
R, R₁, R₂ and A have the meaning indicated there and X represents a —CH₂— groups,
it is possible to obtain carboxyalkylaminoalkylenephosphonic acids of the formula $$HOOC-(CH_2)_n-NH-R-P(=O)(OH)_2 \quad \text{VIII}$$

in which
n represents a rational number from 3 to 5,
which can be used as complex-forming agents and intermediate products.

The parts indicated in the examples which follow are parts by weight, unless stated otherwise.

EXAMPLE 1

136 parts of trimethyl phosphite were heated to 70°-80°. At the same temperature, 134 parts of N-chloromethylpyrrolidone were slowly added dropwise and the methyl chloride produced was collected in a cold trap. After completion of the reaction, 47 parts of methyl chloride had collected in the cold trap. The reaction mixture was distilled in vacuo. 168 parts of the compound of the formula

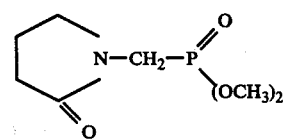

were obtained as a colourless liquid of boiling point$_{0.1}$: 122°–126° and refractive index $n_D^{20}$ 1.4807.

C$_7$H$_{14}$NO$_4$P (207); Calculated: N: 6.76% P: 15.0%; Found: N: 6.78% P: 14.1%.

100 parts of the compound described above were boiled with 400 ml of concentrated hydrochloric acid for 16 hours under reflux. The solution was evaporated in vacuo and the residue was heated for 1 hour to 130°–140° under a pressure of 0.5 mm Hg. On stirring with 300 parts of ethanol, crystallisation occurred. After filtering off, 82 parts of a colourless crystalline compound were obtained; this compound was additionally recrystallised twice from acetonitrile/H$_2$O.

Melting point: 142°–145°.

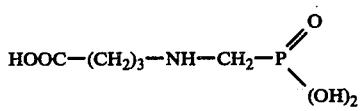

C$_5$H$_{12}$NO$_5$P (197); Calculated: C: 30.45% H: 6.14% N: 7.11% P: 15.7%; Found: C: 30.8% H: 6.3% N: 7.1% P: 16.0%.

EXAMPLE 2

In the same manner, 217 parts of the compound of the formula

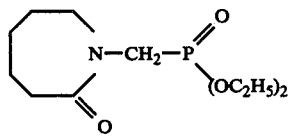

were obtained from 183 parts of triethyl phosphite and 162 parts of N-chloromethylcaprolactam, as a colourless liquid of boiling point$_{0.1}$: 133°–134° and refractive index $n_D^{20}$: 1.4779.

C$_{11}$H$_{22}$NO$_4$P (263); Calculated: N: 5.32% P: 11.79%; Found: N: 5.43% P: 11.9%.

100 parts of the compound described above were boiled with 400 parts of concentrated hydrochloric acid for 18 hours under reflux. The solution was completely evaporated in vacuo and the residue was heated for 1 hour to 130°–140° under a pressure of 0.5 mm Hg. 91 parts of a highly viscous liquid were obtained; the liquid crystallised after dissolving in 110 parts of water. The crystalline product was recrystallised once from acetonitrile/water, and again from ethanol/water. Colourless crystals of melting point 212°–215°.

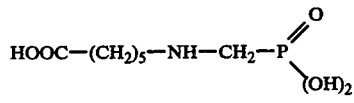

C$_7$H$_{16}$NO$_5$P (225.2); Calculated: C: 37.3% H: 7.2% N: 6.2% P: 13.8%; Found: C: 37.7% H: 7.2% N: 6.3% P: 14.0%.

EXAMPLE 3

In the same manner as that described in Example 1, 384 parts of the compound of the formula

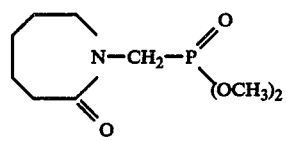

are obtained from 338 parts of trimethyl phosphite and 445 parts of crude N-chloromethyl-caprolactam, as a colourless liquid of boiling point$_{0.35}$: 147°–150° and refractive index $n_D^{20}$: 1.4858.

C$_9$H$_{18}$NO$_4$P (235); Calculated: N: 5.96% P: 13.2%; Found: N: 5.7% P: 13.9%.

EXAMPLE 4

In the same manner as that described in Example 1, 212 parts of the compound of the formula

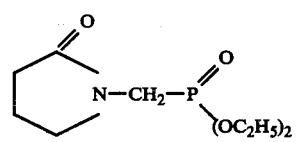

are obtained from 166 parts of triethyl phosphite and 134 parts of N-chloromethylpyrrolidone at 110°–120°, as a colourless liquid of boiling point$_{0.08}$: 110°–112° and refractive index $n_D^{20}$: 1.4705.

C$_9$H$_{18}$NO$_4$P (235); Calculated: N: 5.96% P: 13.2%; Found: N: 5.85% P: 13.2%.

EXAMPLE 5

555 parts of N-chloromethyloxazolidone are slowly added dropwise to 560 parts of trimethyl phosphite at 70°–80° C. The methyl chloride formed is passed through a reflux condenser into a receiver cooled with solid carbon dioxide. After completion of the addition, the mixture is stirred for a further hour at 90°–100° and the product obtained is freed from volatile constituents in vacuo. 890 parts (97% of theory) of the compound

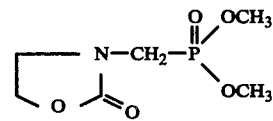

are obtained as a colourless liquid.

C$_6$H$_{12}$NO$_5$P (209) $n_D^{20}$: 1,4700; Calculated: C 35.5% H 5.75% N 6.7% P 14.85%; Found: C 35.2% H 5.8% N 6.9% P 14.9%.

EXAMPLE 6

87 parts of oxazolidone-(2) were dissolved in 200 parts of toluene and 4 parts of a 5.5 molar sodium methylate solution in methanol were added. 164 parts of vinylphosphonic acid diethyl ester were added dropwise at 50°–60° whilst keeping the reaction temperature at the stated level by cooling. After completion of the addition, the mixture was stirred for a further 2 hours at 55°–60°. After neutralisation with hydrochloric acid, the salt which had separated out was filtered off and the filtrate was freed from the solvent in vacuo. Volatile constituents were distilled off by subsequent heating to 170°–180° in the vacuum from an oil pump. 210 parts of the compound

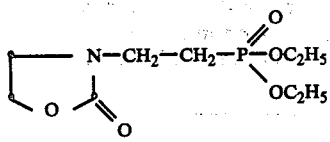

were obtained as a brownish liquid.

C$_9$H$_{18}$NO$_5$P (251) $n_D^{20}$: 1.4700; Calculated: C: 43.1%; H: 7.17%; N: 5.58%; O: 31.9%; P: 12.3%; Found: C: 42.6%; H: 7.2%; N: 5.9%; O: 31.4%; P: 12.5%.

EXAMPLE 7

87 parts of oxazolidone-(2) were dissolved in 180 parts of tert.-butanol at 80°, the solution was cooled to 10°–20° and 5 parts of a 5.5 molar sodium methylate solution were added. 136 parts of vinylphosphonic acid dimethyl ester were then added dropwise whilst keeping the temperature at 20°–25° by cooling. After stirring for 3 hours at 20°–25°, the mixture was neutralised with hydrochloric acid and filtered. The solvent was distilled from the filtrate in a waterpump vacuum at 40°–45°. The residue was freed from volatile constituents in a thin layer evaporator under a vacuum of 1 mm Hg and at a temperature of 190°–200°. 146 parts of the compound

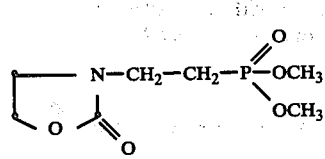

were obtained as a brownish liquid.

C$_7$H$_{14}$NO$_5$P (223) $n_D^{20}$: 1.4760 Calculated: C: 37.7%; H: 6.28%; N: 6.28%; O: 35.9%; P: 13.9% Found: C: 38.2%; H: 6.3%; N: 6.5%; O: 36.1%; P: 13.1%.

EXAMPLE 8

2 parts of a 40% strength solution of benzyltrimethylammonium hydroxide in methanol were added to 85 parts of pyrrolidone-(2). 136 parts of vinylphosphonic acid dimethyl ester were added dropwise over the course of one hour at 25°–30°, whilst cooling. During the addition of the vinyl phosphonic acid dimethyl ester, a pH value of 8–8.5 was maintained in the reaction mixture by occasional addition of 1–2 parts of the benzyltrimethylammonium hydroxide solution. Thereafter the mixture was stirred for a further hour at 25°–30° and pH 8–8.5. In total, a further 4 parts of the benzyltrimethylammonium hydroxide solution were added. The reaction mixture was neutralised with hydrochloric acid and then distilled in vacuo. After a first running, 178 parts of the compound

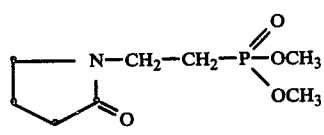

were obtained as a colourless liquid of boiling point$_{0.6}$: 160°–162°.

C$_8$H$_{16}$NO$_4$P (221) $n_D$: 1.4812; Calculated: C: 43.4%; H: 7.24%; N: 6.33%; O: 28.9%; P: 14.0%; Found: C: 43.6%; H: 7.5%; N: 6.5%; O: 28.3%; P: 14.4%.

EXAMPLE 9

2 parts of a 5.5 molar sodium methylate solution were added to a mixture of 113 parts of caprolactam and 136 parts of vinylphosphonic acid dimethyl ester at room temperature, whilst keeping the temperature at 50°–55° by cooling. A pH value of 9–10 was maintained, by slow dropwise addition of sodium methylate solution, up to the end of the exothermic reaction. In total, 12 parts of the sodium methylate solution were consumed. After cooling, insoluble constituents were filtered off and the clear filtrate was freed from volatile constituents by heating to 170°–180° in the vacuum from an oil pump. 230 parts of a yellowish-coloured, slightly viscous liquid remained; this liquid distilled at 168°–170° / 0.5 mm Hg.

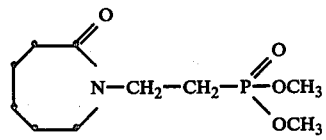

C$_{10}$H$_{20}$NO$_4$P (249) $n_D^{20}$: 1.4849; Calculated: C: 48.2%; H: 8.03%; N: 5.62%; O: 25.7%; P: 12.4%; Found: C: 47.8%; H: 8.0%; N: 5.7%; O: 26.0%; P: 12.5%.

EXAMPLE 10

940 parts of N-(2-chloroethyl)-oxazolidone-(2) were mixed with 400 parts of dimethylformamide and 870 parts of trimethyl phosphite were added slowly at 150°–160°, whilst stirring. After the evolution of gas has ceased, the solvent is distilled off in vacuo. 1,170 parts of the compound

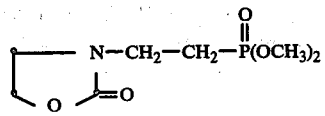

are obtained as a light brown liquid.

C$_7$H$_{14}$NO$_5$P (223) $n_D^{20}$: 1.4790; Calculated: C: 37.7%; H: 6.28%; N: 6.28%; P: 13.9%; Found C: 38.5%; H: 6.3%; N: 7.0%; P: 13.1%.

EXAMPLE 11

332 parts of N-chloromethyl-oxazolidone-2 are added slowly to 271 parts of triethyl phosphite at 100°–110°, whilst collecting the resulting ethyl chloride in a cold trap. After completion of the addition, the reaction mixture is heated to 130° for a further ½ hour and is subsequently freed from volatile constituents at the same temperature in a vacuum of down to 1 mm Hg. 430 parts of the compound

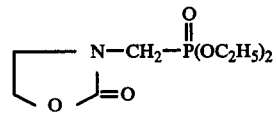

are obtained as a pale yellow liquid.

C$_8$H$_{16}$NO$_5$P (237) $n_D^{20}$: 1.4677; Calculated: C: 40.6%; H: 6.75%; N: 5.91%; P: 13.1%; Found: C: 40.6%; H: 6.7%; N: 6.2%; P: 12.8%.

EXAMPLE 12

270 parts of tris-(2-chloroethyl) phosphite are added slowly to 134 parts of N-chloromethyloxazolidone-(2) at 80°–90° in a flask evacuated to 30–40 mm Hg. The ethylene chloride produced in the reaction is collected in a cold trap cooled to −70°. After completion of the addition the mixture is additionally heated for 1 hour to 90°–100°, a total of 75 parts of ethylene chloride being collected. After removing the volatile constituents under a vacuum of down to 2 mm Hg, 318 parts of the compound

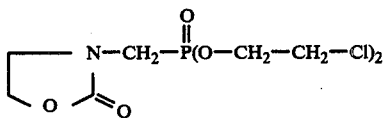

remain as a light brown, viscous liquid.
$C_8H_{14}Cl_2NO_5P(306)$ $n_D^{20}$: 1.4992;
Calculated: C: 31.35%; H: 4.57%; N: 4.57%; Cl: 23.2%; P: 10.1%; Found: C: 31.5%; H: 4.7%; N: 4.6%; Cl: 23.8%; P: 10.3%.

EXAMPLE 13

A fabric of polyethylene terephthalate fibres is impregnated with an aqueous liquor which contains, per liter, 200 g of the product described in Example 5, 30 g of dicyandiamide, 5 g of phosphoric acid and 0.5 g of a reaction product of 1 mol of nonylphenol with 10 mols of ethylene oxide. The impregnated fabric is squeezed off to a weight pick-up of about 80%, dried for 10 minutes at 100° and fixed for 5 minutes at 160°. The fabric is then rinsed with a dilute sodium carbonate solution at 40°, and dried.

The fabric finished in this way was subjected to the vertical test according to DIN 53,906 in order to test its flameproofing properties. The results of the test are listed in the table which follows:

|   | Length burnt | |
| --- | --- | --- |
|   | Warp | Weft |
| A Untreated | Completely burnt | |
| B Finished according to Example 13 | 4.4 cm | 4.5 cm |
| C B, after 10 machine washes at 60° | 5.1 cm | 5.8 cm |

EXAMPLE 14

An aqueous liquor which contains 250 parts of the product described in Example 7, 30 parts of dicyandiamide and 5 parts of phosphoric acid per liter is prepared. A fabric of polyethylene terephthalate fibres is impregnated with this liquor, squeezed off to a weight pick-up of about 80%, dried for 10 minutes at 100° and heated for 5 minutes to 160°. The fabric is then washed for 10 minutes with a solution of 1 part of sodium carbonate per liter at 40°, and is dried.

The fabric finished in this way was tested in accordance with the DIN No. 53,906 vertical test.

|   | Length burnt | |
| --- | --- | --- |
|   | Warp | Weft |
| A Untreated | Completely burnt | |
| B Finished according to Example 14 | 5.6 cm | 5.8 cm |
| C B, after 10 machine washes at 60° | 6.8 cm | 7.2 cm |

We claim:
1. Compound of the formula

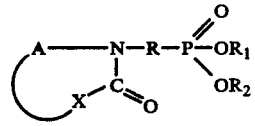

in which
$R_1$ and $R_2$ independently of one another are alkyl with 1–4 C-atoms or alkyl of 1–4 C-atoms substituted by chlorine or bromine;
A and X conjointly with the nitrogen atom and the carbonyl group form an oxazolidone, benzoxazolinone or dihydro oxazinone ring which is unsubstituted; and
R is alkylene with 2–4 carbon atoms.

2. Compounds according to claim 1, of the formula

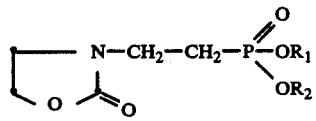

in which
$R_1$ and $R_2$ represent methyl or ethyl.

3. Compound of claim 1 in which
A is 1,2-ethylene or 1,2-propylene; and
X is oxygen.

4. Compound of claim 1 in which R is ethylene.

5. The compound of claim 3 having the formula

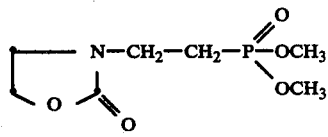

6. Compound of claim 1 in which
R is 1,2-ethylene;
$R_1$ and $R_2$ are methyl, ethyl or 2-chloroethyl;
X is O; and
A is 1,2-ethylene, 1,2-propylene or 1,4-butylene.

* * * * *